United States Patent [19]
Wieczorek

[11] Patent Number: 5,130,093
[45] Date of Patent: Jul. 14, 1992

[54] CLEANING AND STERILIZING MACHINE FOR ARTICLES, SUCH AS CLOSURE ELEMENTS FOR PHARMACEUTICAL CONTAINERS

[75] Inventor: Joachim Wieczorek, Willich, Fed. Rep. of Germany

[73] Assignee: Smeja GmgH & Co. KG, Straelen-Herongen, Fed. Rep. of Germany

[21] Appl. No.: 460,397

[22] Filed: Jan. 3, 1990

[30] Foreign Application Priority Data

Sep. 20, 1989 [DE] Fed. Rep. of Germany ....... 3931368

[51] Int. Cl.$^5$ .......................... A61L 2/06; A61L 2/00; B08B 3/04
[52] U.S. Cl. ...................... 422/26; 422/292; 422/300; 422/302; 134/104.3; 134/134; 134/200
[58] Field of Search ....... 422/26, 32, 33, 295, 422/300, 302, 38, 139, 292; 34/57 A; 134/104.3, 134, 200; 366/235, 220; 426/521

[56] References Cited

U.S. PATENT DOCUMENTS

| | | | |
|---|---|---|---|
| 3,088,179 | 5/1963 | Leuthner | 426/521 |
| 3,514,329 | 5/1970 | Hull | 134/200 |
| 3,992,148 | 11/1976 | Shore et al. | 426/521 |
| 4,059,919 | 11/1977 | Green | 47/1.1 |
| 4,234,537 | 11/1980 | Hersom et al. | 422/26 |
| 4,372,686 | 2/1983 | Herfeld | 366/235 |

FOREIGN PATENT DOCUMENTS

| | | |
|---|---|---|
| 2154582 | 6/1972 | Fed. Rep. of Germany . |
| 2739169 | 3/1979 | Fed. Rep. of Germany . |
| 2801568 | 7/1979 | Fed. Rep. of Germany ...... 422/302 |
| 3248555 | 7/1984 | Fed. Rep. of Germany . |
| 2829381 | 9/1984 | Fed. Rep. of Germany ........ 422/26 |
| 2212386 | 7/1989 | United Kingdom . |
| 2212387 | 7/1989 | United Kingdom . |

OTHER PUBLICATIONS

Brochure, Pharma Clean by Smeja Pharma-Technik, pp. 1-11 (1988/89).

Primary Examiner—Robert J. Warden
Assistant Examiner—Theresa A. Trembley
Attorney, Agent, or Firm—Marmorek, Guttman & Rubenstein

[57] ABSTRACT

The invention relates to a cleaning and sterilizing machine for small articles, such as the closure elements for pharmaceutical containers. The machine consists of a treatment vessel which is mounted in a carrier to pivot through 180° around a horizontal axis, which has a funnel-shaped lower portion comprising a closable discharge opening and to which supply and discharge lines for at least one treatment medium are connected. The discharge opening can be closed by a valve and is also constructed as a charging opening with a coupling member. Connectable in sealing-tight and supporting manner to said coupling member is a charging and discharging container for the articles to be treated which has a matching coupling member disposed at a charging and discharge opening closable by a valve in a funnel-shaped upper portion of the charging and discharge container.

7 Claims, 5 Drawing Sheets

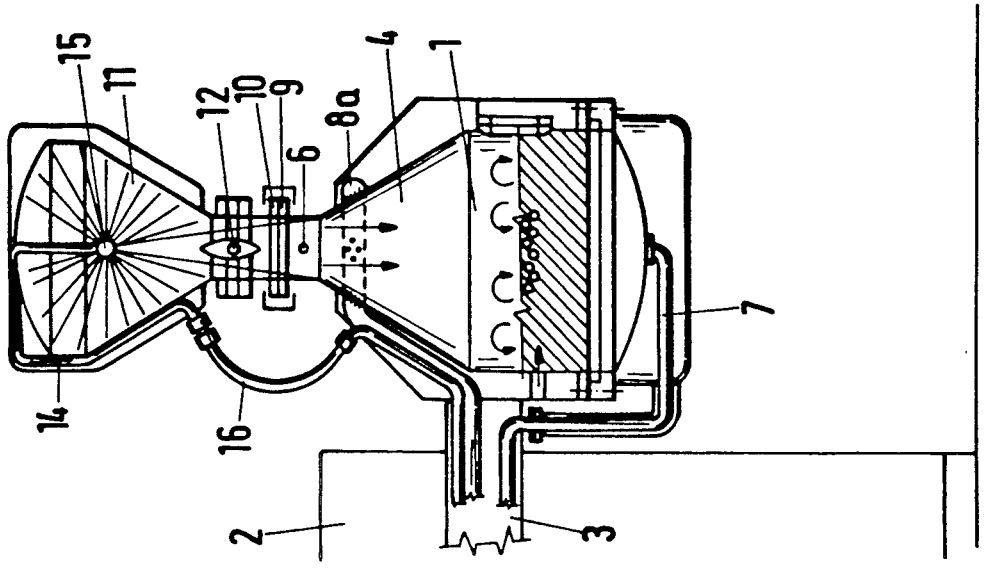
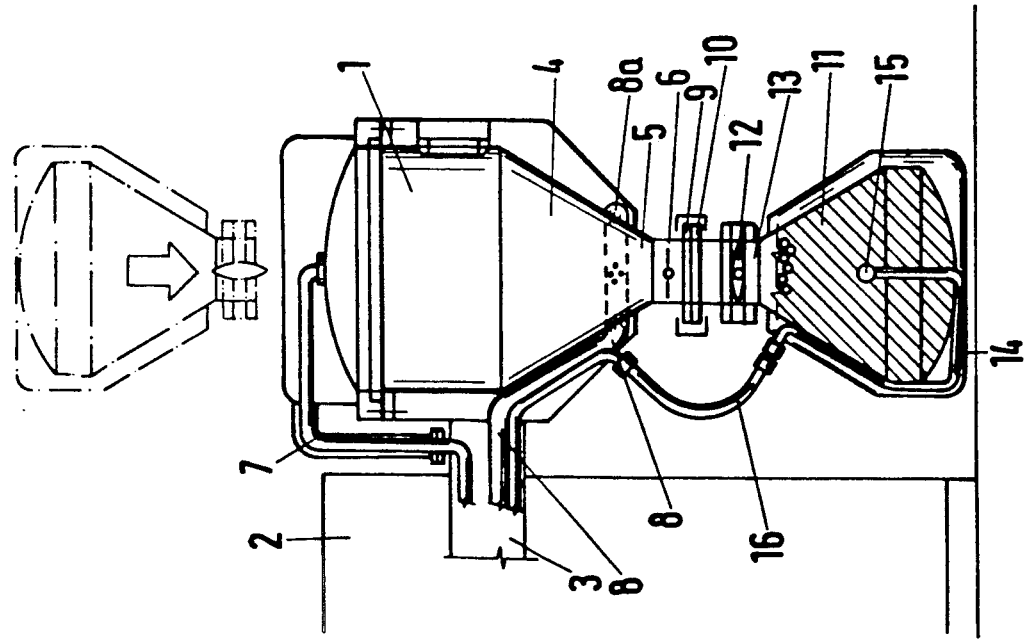

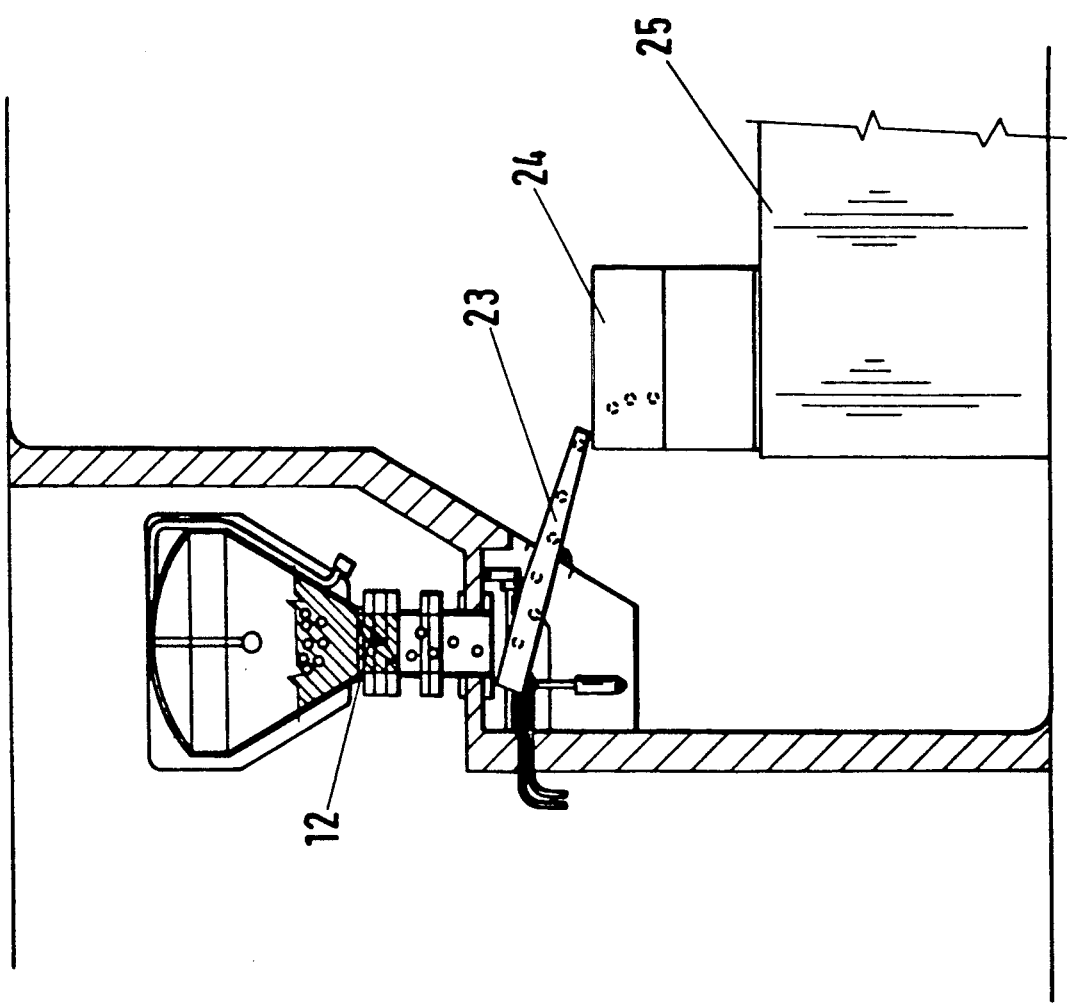

CLEANING AND STERILIZING MACHINE FOR ARTICLES, SUCH AS CLOSURE ELEMENTS FOR PHARMACEUTICAL CONTAINERS The invention relates to a cleaning and sterilizing machine for small articles, such as closure elements for pharmaceutical containers, comprising a treatment vessel which is mounted in a carrier to pivot through 180° around a horizontal axis and which has a funnel-shaped lower portion comprising a closable discharge opening and to which supply and discharge lines for at least one treatment medium are connected.

DESCRIPTION OF THE PRIOR ART

Cleaning and sterilizing machines of the kind specified are known. In one prior art cleaning and sterilizing machine of this kind the treatment vessel is connected to a suction line which extends out of the sterile chamber and via which the treatment vessel can be charged with the articles to be treated, which are supplied from outside the sterile chamber. To discharge the treated articles, the treatment vessel is pivoted through 180°. An operator in the sterile chamber removes a cover from the discharge opening and fills the sterilized articles into a container driven under the discharge opening. Due to the charging of the treatment vessel via the suction line and the manual discharge required in a sterile chamber, the treatment is not only labor-intensive, but also requires a large amount of expensive apparatus.

SUMMARY OF THE INVENTION

It is an object of the invention to provide a cleaning and sterilizing machine which requires only a comparatively small amount of apparatus in the sterile chamber and more particularly renders it unnecessary to accommodate the treatment vessel in a sterile chamber. Other objects of the invention are to substantially mechanize the charging and discharging operations of the cleaning and sterilizing machine and to provide the method of cleaning and sterilizing small articles by the use of the cleaning and sterilizing machine according to the invention.

To this end, in a cleaning and sterilizing machine of the kind specificed, the discharge opening can be closed by a valve and is also constructed as a charging opening with a coupling member. Connectable in sealing-tight and supporting manner to said coupling member is a charging and discharging container for the articles to be treated which has a matching coupling member disposed at a charging and discharging opening closable by a valve in a funnel-shaped upper portion of the charging and discharging container.

The cleaning and sterilizing machine according to the invention need no longer be accomodated in or on a sterile chamber. The same container which receives the non-sterile articles to be cleaned also receives the cleaned and sterilized articles after their treatment in the treatment vessel. This can be done, since after the container has been connected to the treatment vessel it is hermetically sealed together therewith and its interior, like that of the treatment vessel, is cleaned and sterilized during the treatment of the articles. The suction line otherwise extending from the sterile chamber to the treatment vessel and required for the treatment is rendered unnecessary.

After the treatment vessel with the container attached supportingly thereto has been pivoted, the articles to be treated drop out of the container into the treatment vessel, which is then below the container. Conversely, after the treatment vessel has been pivoted again, the articles are emptied into the container. After the container filled with sterilized articles has been closed, it is disconnected from the treatment vessel and can be conveyed to the place of use of the articles.

If the sterilized articles in the container are to be subdivided into smaller units, according to one feature of the invention the charging and discharging container can be connected inverted and in a sealing-tight and supporting manner via its coupling member to a matching coupling member of a lock, leading to a sterile room, of a discharge and transfer device, coupling side cleaning and sterilizing members being disposed in the lock, which can be closed by a bottom cover. After the container has been connected, with the container valve still closed and the lock bottom cover closed, the interior of the lock and the contaminated side of the container valve can be cleaned and sterilized, the bottom cover then being opened and the container valve actuated to enable the sterilized articles to be discharged.

The invention also relates to a method of cleaning and sterilizing small articles, such as closure elements for pharmaceutical containers using the cleaning and sterilizing machine according to the invention. The method is characterized in that when the articles have been transferred from the container to the treatment vessel connected sealing-tight to the container, the articles are treated in the treatment container and the empty container is cleaned and sterilized parallel therewith, whereafter with the treatment vessel connected the cleaned and sterilized articles are transferred to the container, and after the container has been closed it is disconnected from the treatment vessel and connected to the lock which leads to the sterile room and via which the cleaned and sterilized particles, after the cleaning and sterilization of the closed space between the discharging and charging opening and the lock, are emptied into the sterile room.

BRIEF DESCRIPTION OF THE DRAWINGS

FIG. 1 is a perspective view of the treatment vessel connected to the charging and discharging container.

FIG. 2 is a perspective view of the treatment vessel and connected charging and discharging container pivoted 180° to begin treatment of the articles.

FIG. 8 shows the transferring of articles to a sorting and filling machine.

DETAILED DESCRIPTION OF THE PREFERRED EMBODIMENTS

Figure 7:
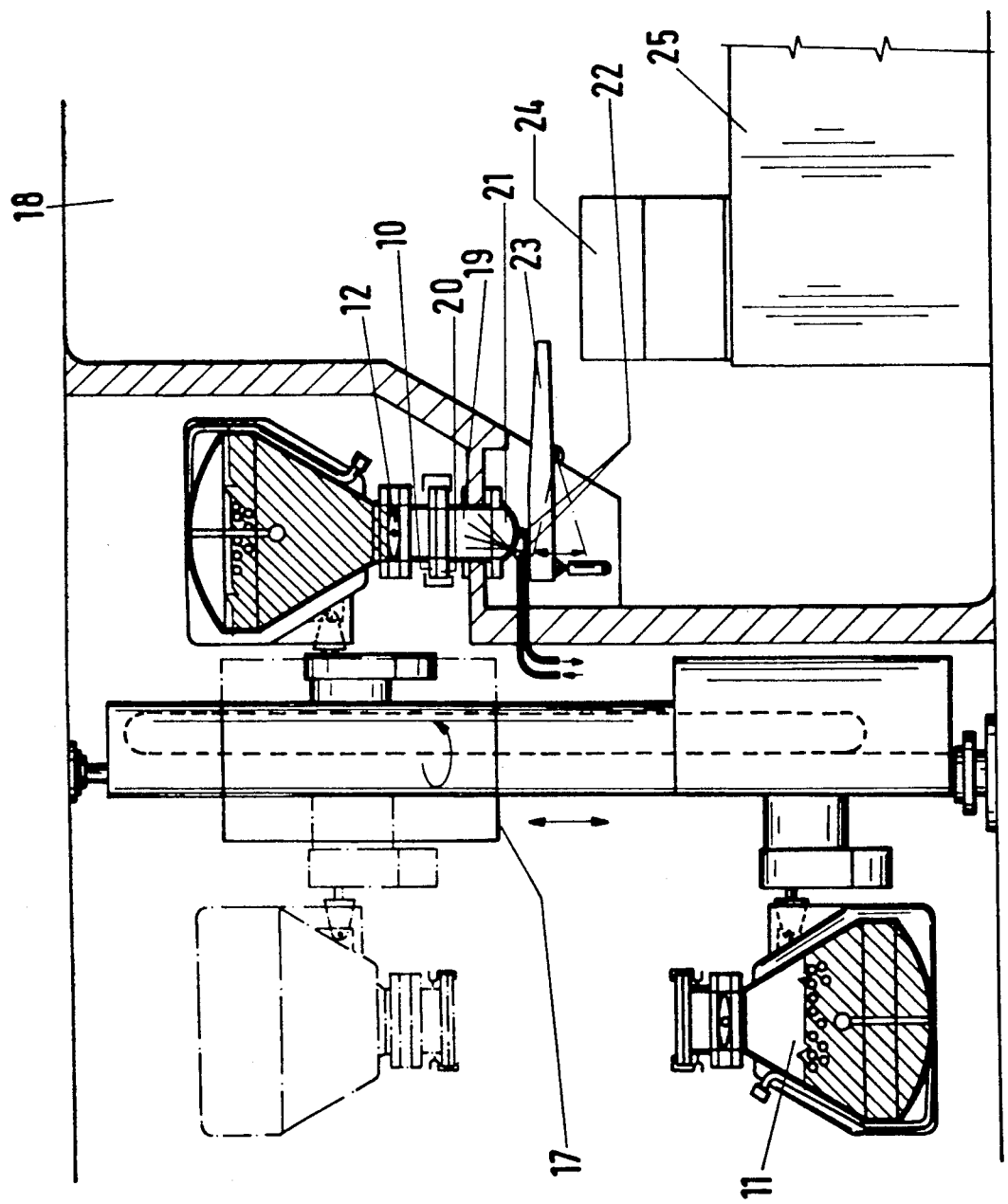
FIG. 7 shows the transferring of sterilized articles to another location for their intended use.

The invention will now be explained in greater detail with reference to the accompanying drawings, wherein FIGS. 1–6 show the inventive cleaning and sterilizing machine during different phases of operation, and wherein FIGS. 7–8 show the inventive cleaning and sterilizing machine in conjunction with a transfer device.

A cleaning and sterilizing machine set up in unsterilized surroundings has a treatment vessel 1 mounted on a machine casing carrier 2 to a pivot through 180° around a horizontal axis 3. The treatment vessel 1 has a funnel-shaped lower portion 4 having a charging and discharging opening 5 closed by a pivotable flap valve 6. Supply and discharge lines 7, 8 for treatment media are connected to the treatment vessel 1. Treatment is performed in known manner using water, steam, hot air and if necessary a silicone dispersion. Hereinafter only a brief description will be given of the treatment and of the special way in which the treatment media pass through the treatment vessel to clean the articles thoroughly and gently, as both are well known.

On the side remote from the treatment vessel, the discharge opening 5 has a coupling member 9, to which a charging and discharging container 11 containing the articles to be cleaned can be connected in a sealing-tight and supporting manner via a matching coupling member 10. The charging and discharging container 11 has funnel-shaped upper portion 13 having a charging and discharging opening which can be closed by a flap valve 12. A line 14 having a distributor nozzle 15 for the treatment media water, steam or compressed air leads into the charging and discharging container 11. A hose 16 extending from the media connections in the machine casing 1 can be connected to the line 14.

FIG. 1 shows the cleaning and sterilizing machine immediately after the charging and discharging container 11 has been connected to the treatment vessel 1. The flap valves 6, 12 are still closed.

FIG. 2 shows the machine after the unit 1, 11 has been pivoted through 180°. The two flap valves 6 and 12 are opened, and the articles to be treated have already been emptied out of the charging and discharging container 11 into the treatment vessel 1. Thge container 11 is cleaning by spraying its walls with hot water supplied via the distributor nozzle 15. The water flows into the treatment vessel 1, in which at the same time the articles are cleaned in a steam fluidized bed by hot steam supplied via the line 7.

Figure 3:
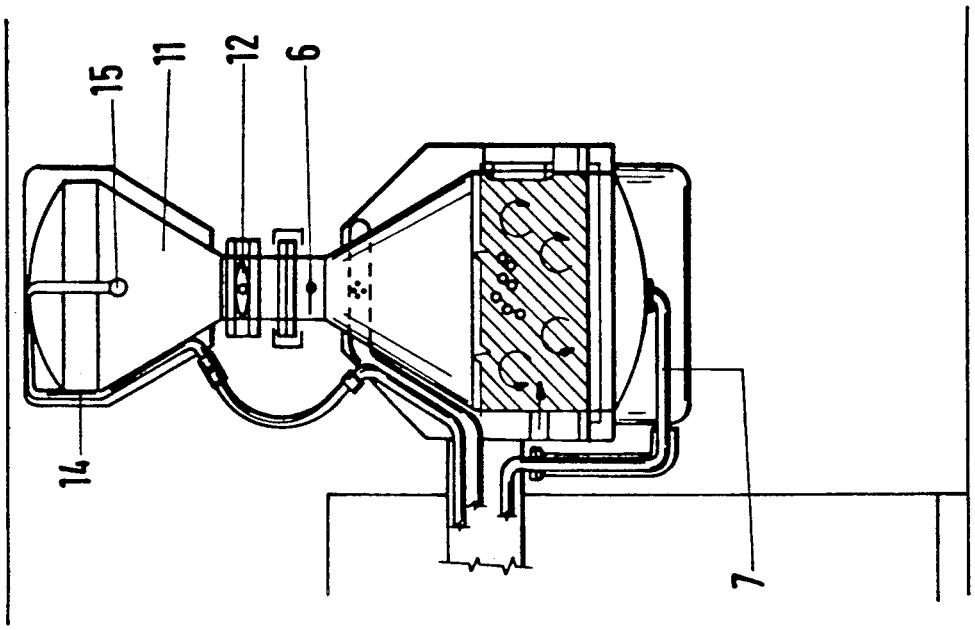
FIG. 3 shows the articles being flushed with water during the initial part of the treatment stage.

In the treatment stage illustrated in FIG. 3 the cleaning of the charging and discharging container 11 with hot water continues, while the treatment vessel 1 is flushed with water removed via an overflow mechanism 8a and line 8.

Figure 4:
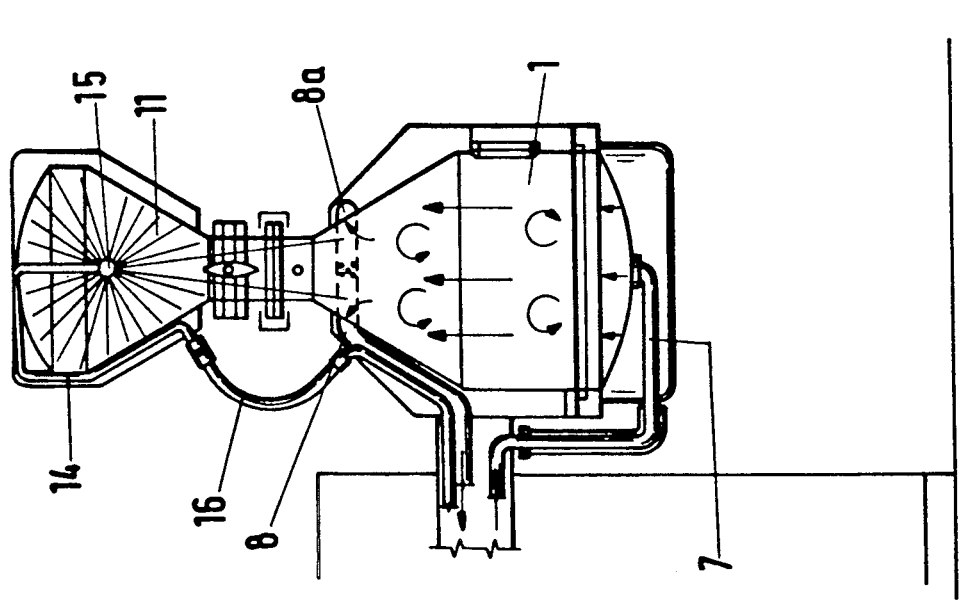
FIG. 4 shows the siliconization of the articles during another part of the treatment stage.
Figure 6:
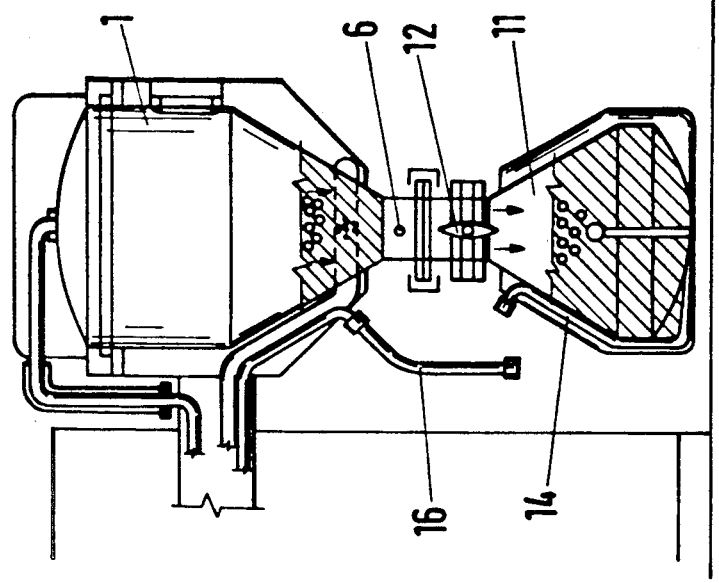
FIG. 6 is a perspective view of the treatment vessel and connected charging and discharging vessel pivoted 180° to their original position.

In the treatment stage illustrated in FIG. 4 the flap valves 6, 12 are closed. The articles are siliconized with a silicone dispersion in the fluidized bed at 100° C. On completion of siliconization, the valves 6, 12 are opened and the silicone dipersion is forced downwards by compressed air supplied via the line 14 with distributor valve 15 and removed via line 7.

Figure 5:
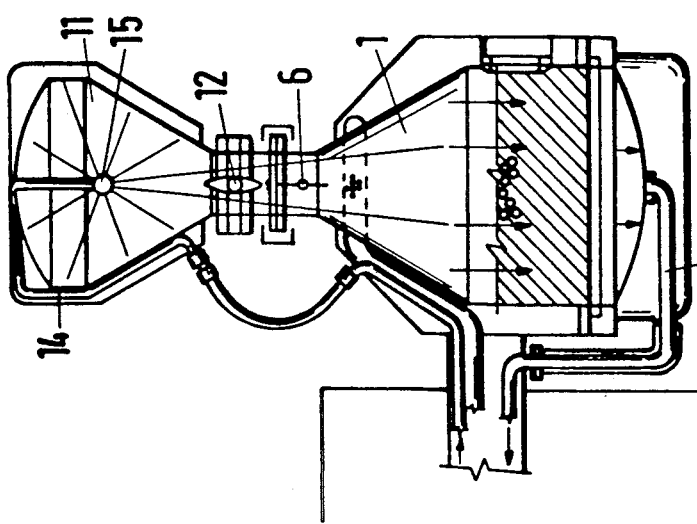
FIG. 5 shows the application of steam to the articles in the final stage of the treatment stage.

In the treatment phase illustrated in FIG. 5 the flap valves 6, 12 are opened and firstly extremely high-purity steam is supplied via line 14 with the distributor valve 15 to the charging and discharging container 11 and the treatment vessel 1 to sterilize the articles of the treatment vessel 1 and the charging and discharging container 11, the steam being drawn off via the lower line 7, so that the flow of steam covers all the articles. On completion of sterilization, the valves 6, 12 are opened, and in the following phase sterile-filtered and headed compressed air is supplied via the line 14 with distributor valve 15 to the charging and discharging container 11 and the treatment vessel 1, to dry the articles of the treatment vessel 1 and the charging and discharging container 11, the compressed air being removed by vacuum suction via line 7, so that the airflow covers all the articles.

To empty the treatment vessel 1 into the charging and discharging container 11 (cf. FIG. 6), the whole unit is again pivoted through 180°. When all the articles are in the charging and discharging container 11, the flap valves 6, 12 are closed, and the line 14, which has a self-closing closure, is separated from the line 16. The charging and discharging container 11 is then disconnected from the treatment vessel 1. The cleaned and sterilized articles are then hermetically sealed in the charging and discharging container 11, which is itself localized in unsterilized surroundings.

To transfer the sterilized articles to other sterile containers and/or to sort them or use them as closures in a filling machine, as shown in FIG. 7 a lifting and rotating platform is provided which has a discharge and transfer device. To this end the closed charging and discharging container 11 is lifted by the lifting and rotating platform 17 and pivoted through 180° around a horizontal axis to above a lock 19 extending to a sterile room 18 and forming part of the discharge and transfer device 23. The lock 19 has a coupling member 20 which is identical to the coupling member 9 of the treatment vessel 1, so that the charging and discharging container 11 can be connected thereto in a sealing-tight and supporting manner via its coupling member 10. In the direction of the sterile room 18, the lock 19 is closed by a bottom cover 21 and equipped with cleaning and sterilizing members 22 by which, when the charging and discharging container 11 has been connected, the space between the flap valve 12 and the bottom cover 21 can be sterilized. On completion of sterilization, the bottom cover 21 can be removed from the lock 19, as shown in FIG. 8. When the flap valve 12 has been opened, the sterilized articles are taken via a transfer device 23 to a sorting machine 24 and a filling machine 25. This obviates the need for an operator to laboriously transfer the sterilized articles from the treatment vessel 1 to a charging and discharging container 11 located in a sterilized room.

What is claimed is:

1. A cleaning and sterilizing machine for small articles such as closure elements for pharmaceutical containers, comprising a treatment vessel in which articles such as closure elements for pharmaceutical containers are to be treated, said treatment vessel having a funnel-shaped lower portion terminating in a first opening and a first valve which opens and closes said first opening, at least one supply line and at least one discharge line connected to said treatment vessel for introducing into and removing from said treatment vessel at least one treatment medium, a charging and discharging container by means of which said articles are introduced into and removed from said treatment vessel, said charging and discharging container having a funnel-shaped upper portion terminating in a second opening and a second valve which opens and closes said second opening, a carrier in which said treatment vessel and said charging and discharging container are mounted in a first position in which said treatment vessel is on top of said charging and discharging container, and in which said vessels are pivotable through 180° around a horizontal axis so as to assume a second position in which said charging and discharging container is on top of said treatment vessel, and coupling means for connecting said treatment vessel to said charging and discharging container in a sealing-tight and supporting manner to form a closed system so that said articles can be introduced into said system via said charging and discharging container when said treatment vessel and said charging and discharging container are in said first position, treated in said treatment vessel when said treatment vessel and said charging and discharging container are in said second position, and removed from said system via said charging and discharging container when said treatment vessel and said charging and discharging container are once again in said first position.

2. the cleaning and sterilizing machine of claim 1 wherein said coupling means comprises a first coupling member attached to said first opening and a second coupling member attached to said second opening, said first and second coupling members being adapted to mate together.

3. The cleaning and sterilizing machine of claim 2 further comprising a sterile room and a transfer device therein, said transfer device having a lock which extends out of said sterile room and includes a third coupling member adapted to mate with said second coupling member of said charging and discharging vessel in a sealing-tight and supporting manner.

4. The cleaning and sterilizing machine of claim 3 further comprising coupling side cleaning and sterilizing members disposed in said lock, and a closable bottom cover for said lock.

5. A method for cleaning and sterilizing small articles such as closure elements for pharmaceutical containers by means of a cleaning and sterilizing machine according to any of claims 1-4, comprising introducing said articles into said system via said charging and discharging container when said treatment vessel and said charging and discharging container are in said first position, pivoting said treatment vessel and said charging and discharging container into said second position thereby causing said articles to be introduced into said treatment vessel, cleaning and sterilizing said articles in said treatment vessel while simultaneously cleaning and sterilizing said charging and discharging container, pivoting said treatment vessel and said charging and discharging container back into said first position thereby causing said articles to be re-introduced into said charging and discharging container, and removing said articles from said system via said charging and discharging container.

6. The method of claim 5 further comprising closing said second valve of said charging and discharging container, disconnecting said charging and discharging container from said treatment vessel, connecting said charging and discharging container to said transfer device in said sterile room via said lock, and emptying said articles into said sterile room.

7. The method of claim 6 further comprising cleaning and sterilizing an empty space in said lock before emptying said articles into said sterile room.

* * * * *